United States Patent
Gadre et al.

(10) Patent No.: US 9,713,592 B2
(45) Date of Patent: Jul. 25, 2017

(54) MATRIX-BASED PULSE RELEASE PHARMACEUTICAL FORMULATION

(75) Inventors: Ashwini Gadre, Brisbane, CA (US); Mark R. Benmuvhar, St. Louis, MO (US); Brian Kai-Ming Cheng, Chesterfield, MO (US); Vishal K. Gupta, Ballwin, MO (US); Cliff J. Herman, St. Louis, MO (US)

(73) Assignee: MALLINCKRODT LLC, Hazelwood, MO (US)

( * ) Notice: Subject to any disclaimer, the term of this patent is extended or adjusted under 35 U.S.C. 154(b) by 1866 days.

(21) Appl. No.: 11/909,270

(22) PCT Filed: Mar. 22, 2006

(86) PCT No.: PCT/US2006/010279
§ 371 (c)(1),
(2), (4) Date: Mar. 19, 2010

(87) PCT Pub. No.: WO2006/107593
PCT Pub. Date: Oct. 12, 2006

(65) Prior Publication Data
US 2010/0166864 A1   Jul. 1, 2010

Related U.S. Application Data

(60) Provisional application No. 60/668,931, filed on Apr. 6, 2005.

(51) Int. Cl.
| A61K 9/14 | (2006.01) |
| A61K 31/131 | (2006.01) |
| A61K 9/16 | (2006.01) |
| A61K 9/24 | (2006.01) |
| A61K 9/20 | (2006.01) |

(52) U.S. Cl.
CPC .............. *A61K 9/167* (2013.01); *A61K 9/209* (2013.01); *A61K 9/1652* (2013.01); *A61K 9/2054* (2013.01)

(58) Field of Classification Search
None
See application file for complete search history.

(56) References Cited

U.S. PATENT DOCUMENTS

| 3,577,512 A | 5/1971 | Shepherd et al. |
| 6,322,819 B1 | 11/2001 | Burnside et al. |
| 6,913,768 B2 * | 7/2005 | Couch et al. ................ 424/490 |
| 2002/0098232 A1 | 7/2002 | Midha et al. |
| 2003/0092724 A1 | 5/2003 | Kao et al. |
| 2003/0235616 A1 * | 12/2003 | Sowden et al. .............. 424/473 |
| 2006/0159753 A1 * | 7/2006 | Ueki et al. ................... 424/468 |

FOREIGN PATENT DOCUMENTS

| WO | WO 93/13773 | 7/1993 |
| WO | WO 02/087512 | 11/2002 |
| WO | WO 2004/071501 | 8/2004 |
| WO | WO 2005/072079 | 8/2005 |

OTHER PUBLICATIONS http://www.thefreedictionary.com/matrix, accessed Oct. 25, 2012.*

* cited by examiner

*Primary Examiner* — Tigabu Kassa

(57) ABSTRACT

The present invention relates to an oral pulse release pharmaceutical composition, which comprises a polymer matrix core, wherein at least one pharmaceutically active ingredient is distributed within the core and on the outer surface of the core. Amphetamine salts, among a number of other pharmaceutically active ingredients, can be formulated as a pharmaceutical composition described herein. The present invention also provides a method for preparing an immediate release component on a solid pharmaceutical formulation.

27 Claims, 1 Drawing Sheet

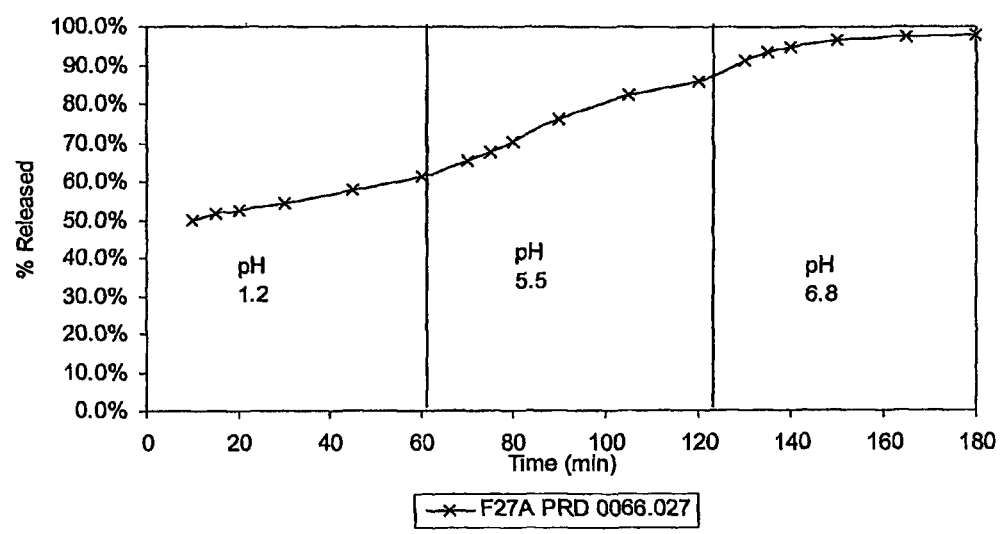

MATRIX-BASED PULSE RELEASE PHARMACEUTICAL FORMULATION

CROSS-REFERENCE TO RELATED APPLICATIONS

This application is a U.S. National Stage Application of PCT International Application No. PCT/US2006/010.279. filed Mar. 22, 2006, which claims priority to U.S. Provisional Application Ser. No. 60/668,931, filed Apr. 6, 2005, the disclosure of each is hereby incorporated by reference in its entirety.

FIELD OF THE INVENTION

The present invention generally relates to an orally administrable pharmaceutical composition comprising a polymer matrix having at least one pharmaceutically active ingredient distributed within and on the outer surface of the matrix. Advantageously, such compositions may be tailored to provide a range of blood plasma profiles.

BACKGROUND OF THE INVENTION

In general, the objective of a drug delivery system is to provide an effective therapeutic amount of a drug to a targeted site in the body to quickly obtain, and then maintain, the desired drug concentration. Two considerations of drug delivery are spatial placement and temporal delivery of a drug; spatial placement relates to the targeting of a drug to a specific organ or tissue, while temporal delivery refers to controlling the rate of drug delivery to the target tissue.

A number of drugs require more than one administration during the day in order to maintain a desirable plasma concentration. One problem experienced with such drugs is that more than one dosing a day can affect patient compliance, especially in pediatric patients. By way of example, ADDERALL®, which is indicated for treatment of Attention Deficit Hyperactivity Disorder in children from 3-10 years of age, has a disadvantage that two separate doses are administered, one in the morning and one approximately 4-6 hours later, commonly away from home under other than parental supervision. This form of treatment, therefore, requires a second treatment which is time-consuming and inconvenient. As another example, the greatest incidence of cardiovascular disorders including angina, stroke, heart attack, etc., typically occur during the early morning hours when blood pressure is rising in response to natural circadian rhythm. Accordingly, there are numerous instances where it would be beneficial to have a formulation which can provide two or more doses, delivered at different times.

A number of various pharmaceutical formulations have been developed to minimize the number of doses required to be taken each day, such as sustained and pulsatile formulations. To a first approximation, sustained release compositions are designed to provide a release of the pharmaceutical over an extended period of time. In contrast, pulsatile release compositions are designed to provide one or more release pulses separated by time and/or sites; for example, a pulsatile release composition may be designed to provide an immediate release pulse in the stomach and a second release pulse, delayed from the first by several hours, in the small intestine. See, e.g., Burnside et al., U.S. Pat. No. 6,322,819 B1.

A number of factors may influence the efficacy of pulse drug release and thus, represent a source of variability. Such factors include the complexity of the process for drug formulation, reproducibility of the manufacturing process, and uniformity of the product produced by the manufacturing process. In addition, gastrointestinal transit times vary not only from patient-to-patient but also within patients as a result of food intake, stress, and illness. Thus, while a variety of pulse release formulations have been proposed in consideration of one or more of these factors, room nevertheless remains for further improvement.

SUMMARY OF THE INVENTION

The present invention relates to an orally administrable pharmaceutical composition comprising at least one pharmaceutically active ingredient and a polymer matrix, wherein the active ingredient is distributed in the matrix and on the outer surface of the matrix. The polymer matrix comprises an enteric polymer and a sustained release polymer, wherein the ratio of the two polymers in the matrix can be varied in order to produce different release profiles. Furthermore, the pharmaceutical composition of the present invention can either utilize the same or different pharmaceutically active ingredients in the matrix and on the outer surface of the matrix. The active ingredient on the outer surface of the matrix provides for immediate release of said active ingredient upon oral administration.

Therefore, among the aspects of the present invention is an oral pharmaceutical composition comprising a polymer matrix, wherein a first pharmaceutically active ingredient is substantially uniformly distributed within the matrix and a second pharmaceutically active ingredient is deposited on the outer surface of the matrix. Generally, the outer surface has been pretreated with a granulating solvent in order to allow the second pharmaceutically active ingredient to adhere thereto. In one embodiment, the first and the second pharmaceutically active ingredients are the same. In another embodiment, the pharmaceutical composition is an oral pulse release pharmaceutical composition. In another embodiment, the pharmaceutically active ingredient comprises a mixture of amphetamine salts. The polymer matrix comprises at least one enteric polymer and at least one sustained release polymer.

The present invention also provides a method for preparing an immediate release component of a pharmaceutical composition. The method involves applying a granulating solvent to an outer surface of a solid pharmaceutical composition, and adhering a pharmaceutically active ingredient onto the outer surface of the composition. The active ingredient on the outer surface is the immediate release component of said composition.

It is another embodiment of the present invention to provide an oral pharmaceutical composition comprising an enteric polymer matrix, wherein a pharmaceutically active ingredient is substantially uniformly distributed throughout the enteric polymer matrix.

Other objects and features will be in part apparent and in part pointed out hereinafter.

BRIEF DESCRIPTION OF FIGURES

FIG. 1 is an in vitro continuum dissolution profile of a pharmaceutical composition described in Example 1.

ABBREVIATIONS AND DEFINITIONS

To facilitate understanding of the invention, a number of terms are defined below:

The term "enteric polymer" is used herein to represent a polymer, whose solubility is dependent on the pH in such a manner that it generally prevents the release of the drug in the stomach but permits the release of the drug at some stage after the formulation has emptied from the stomach.

The term "pharmaceutically acceptable" is used adjectivally herein to mean that the modified noun is appropriate for use in a pharmaceutical product; that is the pharmaceutically acceptable material is relatively safe and/or non-toxic, though not necessarily providing a separable therapeutic benefit by itself.

The term "release profile" refers to the pattern of release of the respective pharmacologically active substance over time, that is, the amount released over time. This may be measured either in vivo, e.g., indirectly by measuring the blood concentration, or preferably ex vivo, e.g., by the USP paddle or basket method that allows for determination of the dissolution rate of the substance.

The term "subject" includes any human or animal. The animal subject can be a domestic livestock species, a laboratory animal species, a zoo animal. The terms "subject" and "patient" are used interchangeably herein.

The term "sustained release polymer" refers to a polymer whose solubility is independent of pH.

The term "therapeutically-effective" is intended to qualify the amount of an agent or combination of two or more agents, which will achieve the goal of improvement in disorder severity and the frequency of incidence over no treatment.

The term "total amount of drug" means the quantity by weight (% w/w) of a drug comprised in the pharmaceutical composition. The term "drug" is used interchangeably with the term "pharmaceutically active ingredient."

The term "treatment" includes alleviation, elimination of causation of or prevention of undesirable symptoms associated with a disease or disorder. Treatment as used herein includes prophylactic treatment.

DETAILED DESCRIPTION OF THE
PREFERRED EMBODIMENTS

Pharmaceutical compositions of the present invention generally comprise a polymer matrix with one or more active pharmaceutical ingredients uniformly distributed within the matrix and deposited on the outer surface of the matrix. By tailoring the composition of the polymer matrix or the distribution of the pharmaceutically active ingredient(s), the plasma appearance profile of the active ingredient(s) may be desirably controlled.

Pharmaceutically Active Ingredients

In general, the pharmaceutical composition of the present invention may be used for oral delivery of any of a range of pharmaceutically active ingredients for which a pulse delivery is desired. For example, the pharmaceutically active ingredient may be amphetamine base, an amphetamine salt, a mixture of amphetamine salts, or a combination thereof. Alternatively, the pharmaceutically active ingredient may be an opioid drug, such as morphine, codeine, oxycodone, hydrocodone, hydromorphone, and meperidine.

In one embodiment of the invention, the composition comprises as the pharmaceutically active ingredient amphetamine base, one or more salts thereof, or a combination thereof. For example, the active ingredient(s) may include (i) methylphenidate, an optically active isomer thereof, a mixture of optically active isomers thereof, one or more salts thereof, or a combination thereof; (ii) phenylpropanolamine, an optically active isomer thereof, a mixture of optically active isomers thereof, one or more salts thereof, or a combination thereof; (iii) another composition indicated for the treatment of attention deficit hyperactivity disorder (ADHD), or (iv) a combination thereof. In one embodiment, for example, the pharmaceutically active ingredient comprises a mixture of dextroamphetamine sulfate, amphetamine sulfate, the dextro isomer of amphetamine saccharate, and d, I-amphetamine aspartate. In one particular embodiment, the combination of amphetamine salts and isomers in each tablet results in a 3:1 ratio of dextroamphetamine: levoamphetamine, as used in ADDERALL® tablets (Shire US Inc., Florence, Ky.).

In general, the pharmaceutically active ingredient(s) are preferably soluble in the polymeric matrix. In addition, and as described in greater detail elsewhere herein, to facilitate manufacturing the pharmaceutically active ingredient(s) are preferably less soluble in the granulating solvent than the polymer matrix. While not being bound to a particular theory, it is believed that this more readily facilitates adhesion of the pharmaceutically active ingredient thereto, while not significantly affecting the pharmaceutically active ingredient that is dispersed throughout the matrix.

Polymeric Matrix

In addition to the pharmaceutically active ingredient(s), the polymer matrix of the present invention contains at least one enteric polymer and at least one sustained release polymer. Enteric polymers that may be used in the oral pulse release pharmaceutical formulation include but are not limited to: hydroxypropyl methylcellulose acetate succinate (HPMCAS), hydroxypropyl methylcellulose phthalate (HP-MCP), polyvinyl acetate phthalate, cellulose acetate phthalate, cellulose acetate trimellitate, shellac, zein, polymethacrylates containing carboxyl groups, amylose acetate phthalate, styrene maleic acid copolymer, and cellulose acetate succinate. Examples of commercially available enteric material are available under the trade names EUDRAGIT® L 100 (methyl methacrylate/methacrylic acid copolymers wherein the ratio of free carboxyl groups to esters is about 1:1), EUDRAGIT® S 100 (methacrylic acid/methyl methacrylate copolymer with a 1:2 ratio of MA to MMA) or EUDRAGIT® L (methacrylic acid/methyl methacrylate copolymer with a 1:1 ratio of MA to MMA). Aqueous colloidal polymer dispersions or re-dispersions can be also applied, e.g. EUDRAGIT® L 30D-55 (methacrylic acid/ethyl acrylate copolymer), EUDRAGIT® L100-55 (ethyl acrylate, methacrylic acid copolymer), EUDRAGIT® preparation 4110D (methacrylic acid/methyl acrylate/ methyl methacrylate copolymers wherein the ratio of methacrylic acid, methyl acrylate and methyl methacrylate monomers is about 1:6.5:2.5); AQUATERIC° (a mixture containing 66-73% of cellulose acetate phthalate (CAP), poloxamer and acetylated monoglycerides), AQUACOAT® CPD 30 (FMC) (30% by weight aqueous dispersion containing cellulose acetate phthalate (CAP) polymer); KOLLICOAT MAE® 30D (ethyl acrylate/methacrylic acid copolymers wherein the ratio of free carboxyl groups to esters is about 1:1) 30DP (BASF) (methacrylic acid/ethyl acrylate copolymer, 30% dispersion); and EASTACRYL® 30D (Eastman Chemical) ((30% polymeric dispersion of methacrylic acid ethyl acrylate copolymer in water). In one embodiment, the enteric polymer is hydroxypropyl methylcellulose acetate succinate (HPMCAS).

Sustained release polymers that may be used for the purposes of the present invention include but are not restricted to: ETHOCEL® FP 10 (ethyl cellulose), EUDRAGIT® RS ((trimethylammoniumethyl methacrylate chloride), EUDRAGIT® RL (trimethylammoniumethyl methacrylate chloride), EUDRAGIT® NE30D (poly(ethylacrylat-methylmethacrylat)-dispersion 30%), hydroxypropyl methylcellulose (HPMC), hydroxyethyl cellulose (HEC), and polyvinyl pyrrolidone (PVP). In one embodiment, the sustained release polymer is ethyl cellulose. In a preferred embodiment, the sustained release polymer is ETHOCEL® FP 10.

In addition to the enteric and sustained release polymers, the matrix preferably additionally comprises at least one binder. Binders are well known in the art of preparing pharmaceuticals, and include compositions such as acacia, alginic acid, carboxymethylcellulose sodium, microcrystalline cellulose, citric acid, dextrin, ethylcellulose, gelatine, glucose, guar gum, hydroxypropyl methylcellulose, methylcellulose, polyethylene oxide, povidone, pregelatinised starch, syrup, polyvinylpyrrolidone, polyvinylpyrrolidone/vinyl acetate copolymer, and the like.

The polymeric matrix may also preferably comprise at least one plasticizer. Exemplary plasticizers include acetyltriethyl citrate, triethyl citrate, acetyltributyl citrate; dibutylsebacate, triacetin, polyethylene glycols, and propylene glycol. In one embodiment, triethyl citrate is preferably included as a plasticizer.

As mentioned above, the pharmaceutical composition preferably comprises a polymer matrix comprising a mixture of enteric and sustained release polymers. For example, the matrix may comprise one enteric polymer and one sustained release polymer. Alternatively, the matrix may comprise two or more enteric polymers and at least one sustained release polymer, or at least one enteric polymer and two or more sustained release polymers. Other combinations, such as a single enteric polymer with two or more sustained release polymers, or a single sustained release polymer with two or more enteric polymers are also encompassed within the present invention. Example 1 describes one such exemplary composition which comprises HPMCAS-L as an enteric polymer and ETHOCEL® Standard FP 10 as a sustained release polymer.

The relative proportions of enteric and sustained release polymers as well as the characteristics of the enteric and sustained release polymers may be varied across a wide range to enable a range of release profiles. In general, however, the enteric polymer preferably constitutes between about 30% w/w and about 80% w/w of the composition; in one exemplary embodiment, the enteric polymer(s) preferably constitute about 55% w/w of the composition. The sustained release polymer(s) constitute between about 5% w/w and about 80% w/w of the composition, and preferably between about 5% w/w and about 20% w/w of the composition. In one exemplary embodiment, the sustained release polymer(s) constitute about 10% w/w of the composition. By way of example, the pharmaceutical composition can contain 8% w/w of ETHOCEL® Standard FP 10, as shown in Example 1.

One skilled in the art will realize that the ratio of enteric polymer(s) and sustained release polymer(s) can be adjusted based on a desired release profile for a particular pharmaceutically active ingredient. For example, the use of the pharmaceutical composition containing 25% w/w amphetamine salts, 55% w/w of HPMCAS-L and 8% w/w ETHOCEL® Standard FP 10 results in a release profile as described in FIG. 1. If a different active ingredient is used that would benefit from a modified release profile, e.g., the release is over a longer period of time, the ratio of enteric/sustained release polymers can be adjusted to accommodate this change. Preferably, to achieve a longer release profile, the amount of the sustained release polymer is increased and the amount of the enteric polymer is decreased. It is also possible to increase the amount of a sustained release polymer while keeping the amount of the enteric polymer constant. In contrast to this, a shorter release profile can be achieved by decreasing the amount of the sustained release polymer and increasing the amount of the enteric polymer. A skilled artisan can readily perform experiments to determine the appropriate amounts of matrix polymers for a particular drug. For example, the same active ingredient can be prepared in a number of different formulation and its dissolution profile studied using, e.g., USP Paddle or Basket Apparatus.

The first and the second pharmaceutically active ingredients are provided in the amount from about 15% w/w to about 40% w/w of the pharmaceutical composition. In one embodiment, the active ingredients are provided in the amount of about 25% w/w. By way of example, when the pharmaceutical composition comprises a mixture of amphetamine salts as a pharmaceutically active ingredient, the amount of amphetamine salts in the composition is 25% w/w. In another embodiment, the matrix comprises about 50% w/w of the total amount of the first and second pharmaceutically active ingredients and the outer surface of the matrix comprises about 50% w/w of the total amount of the first and second pharmaceutically active ingredients.

In still another embodiment, when the pharmaceutical formulation contains amphetamine salts, the formulation is such that about 50% of the salts are released immediately and about 50% of the salts are released at a delayed time. Accordingly, for such formulation, the matrix contains about 50% of the amphetamine salts, and the surface adhered salts account for about 50% of the total amphetamine salts. By way of example, if the pharmaceutical composition contains 20 mg of the amphetamine salts, 10 mg are contained in the matrix and the other 10 mg are distributed on the outer surface of the matrix.

However, it should be noted that the pharmaceutically active ingredient does not have to be evenly distributed in the matrix and on the outer surface of the matrix. For example, the matrix and the outer surface of the matrix may contain different percentages of drug, e.g., the matrix can contain, e.g., 10%, 20%, 30%, 40%, whereas the outer surface of the matrix contains 90%, 80%, and 70% of the drug, respectively. By way of example, when a drug to be formulated is an opiate, such as, e.g., morphine, it is desirable that the matrix include 80%, and that the outer surface includes 20% of the drug.

Furthermore, different active ingredients can be used in the polymer matrix and on the outer surface of the matrix. For example, one can formulate an opioid and an analgesic together, such that opioid is on the outer surface of the matrix, and the analgesic is in the matrix. A large number of analgesics, such as, acetaminophen, acetylsalicylic acid, ibuprofen, and naproxen are well known in the art. A skilled artisan can readily determine suitable drug combinations for the present pharmaceutical composition.

Preparation of the Composition

The pharmaceutical composition of the present invention is preferably prepared in two phases. The first phase involves preparing the matrix with a pharmaceutically active ingredient therein, whereas the second phase involves treating the outer surface of the matrix in order to adhere either the same or a different pharmaceutically active ingredient thereto. Several methods for preparing a matrix formulation are briefly described below as they are generally known in the art.

The first method involves extrusion and spheronization. Briefly, pharmaceutically active ingredient(s) and other additives are granulated by addition of a binder solution. The wet mass is passed through an extruder equipped with a certain size screen ranging from mesh size 10 to mesh size 100, and the extrudates are spheronized in a marumerizer. The resulting pellets are dried and sieved for further applications.

The second method involves high-shear granulation. Pharmaceutically active ingredient(s) and other additives (binders, plasticizer, enteric polymers and sustained release polymers) are dry-mixed and then the mixture is wetted by addition of a binder solution in a high shear-granulator/mixer. The granules are kneaded and sometimes wet-milled. The resulting granules or pellets are dried and sieved for further applications.

By way of example, the granulate mass is next passed through the roller compactor to obtain ribbons or through an extruder in order to form extrudates. The extrudates can then be spheronized to obtain spheres or the ribbons can be milled in order to obtain granules. Following this, the spheres or granules are dried using a fluid bed drier.

Following the preparation of matrices in the form of granules or spheres as described above, the dried spheres/granules are re-granulated with a pharmaceutically active ingredient using a granulating solvent. The pharmaceutically active ingredient is either the same or different from the one in the matrix. Briefly, re-granulation is achieved by spraying the spheres/granules with a re-granulating solvent and mixing with a selected pharmaceutically active ingredient that adheres to the outer sphere/granule surface. Following the treatment with a solvent, the matrix surface may be allowed to dry prior to deposition of the drug on the surface. The drug can be deposited by, e.g., by powder layering in a pan or fluid-bed roto-processor.

While not being bound to a particular theory, it is believed that the re-granulating solvent used to treat the matrix's outer surface acts as a binder, which allows the deposited active ingredient to adhere strongly to it. It is further thought that the pharmaceutically active ingredient on the outer surface of the matrix is deposited as a population of discrete particles of said active ingredient having a size in the range from about 500 nanometers to about 800 microns. Typically, the active ingredient has a size in the range from about 50 microns to about 200 microns. Therefore, while not being bound to a theory, it is believed that the pharmaceutically active ingredient on the outer surface of the matrix forms a discontinuous layer thereon.

The solvent used for granulation and re-granulation can either be the same solvent or a different solvent. It is preferable to use the same solvent for both granulation steps. Furthermore, a hydroalcoholic solvent is preferably used; however, other solvents, such as aqueous or organic solvents may also be utilized.

The granulating solvent is selected based on the solubility criteria of the matrix and the drug. In particular, the solvent used to treat the outer surface of the matrix is selected in such manner to allow dissolution of both polymers, i.e., enteric polymers and sustained release polymers. The solubilization does not need to be complete, i.e. partial solubilization is sufficient. In selecting a solvent, it is also important to consider that the matrix polymers should be more soluble in such solvent than the drug. While not being bound to a particular theory, it is believed that the solvent treatment, e.g. hydroalcoholic granulation as described above, allows for the immediate release drug to be sufficiently bound to the outer matrix surface, thus avoiding the need for use of a protective layer. It is further thought that the solvent treatment dissolves or partially dissolves the outermost surface of the matrix, thus allowing the immediate release drug to embed in such outermost surface.

In one embodiment, the solvent that is used is a hydroalcoholic solvent. The solvents used herein include one or more alcohols in combination with water, thereby producing a hydroalcoholic solvent system. The alcohol used in the compositions of the present invention is a lower chain hydrocarbon alcohol (referred to herein as a "lower alcohol"), particularly a $C_1$-$C_4$ alcohol (i.e., an alcohol having 1-4 carbon atoms). In preferred embodiments, the alcohol is ethanol, 2-propanol (i.e., isopropanol), or n-propanol. In more preferred embodiments, the alcohol is ethanol or isopropanol. isopropanol and ethanol are preferred alcohols because they provide excellent penetration enhancement for a wide variety of pharmaceutical agents. The lower alcohol to water ratio in the compositions of the present invention is at least about 20:80 by weight (i.e., the lower alcohol is present in an amount of at least about 20 weight percent, and the water is present in an amount of about 80 weight percent, based only on the weight of the water plus the lower alcohol within the composition). Typically, the solvents used herein have an alcohol to water ratio of no greater than about 99:1 by weight. Solvents having an alcohol to water ratio within a range of about 30:70 to 80:20 by weight (i.e., 30-80 weight percent alcohol and 20-70 weight percent water, based only on the weight of water plus lower alcohol in the composition) are particularly efficacious. The lower alcohol to water ratio is generally at least about 50:50 and typically no greater than about 90:10. In one embodiment, the hydroalcoholic solvent contains 80% alcohol and 20% water. It should be noted that a solvent to be used in the present invention can readily be determined by a skilled artisan based on the properties of the polymers in the matrix and the pharmaceutically active ingredient(s).

The materials that can be employed in making drug-containing pellets are any of those commonly used in pharmaceutics and should be selected on the basis of compatibility with the active drug and the physicochemical properties of the pellets. The additives that may optionally be used are listed below. Suitable binders have been described above. Disintegration agents such as corn starch, pregelatinlzed starch, cross-linked carboxymethylcellulose (AC-DI-SOL®), sodium starch glycolate (EXPLOTAB®), cross-linked polyvinylpyrrolidone (PLASDONE XL®) can be added to the pharmaceutical formulation described herein if the formulation is to be prepared in a tablet form. Disintegrants are added in order to disperse the beads once the tablet is ingested. Lubricants are also added to assure proper tableting, and the ones that can be used include but are not restricted to calcium stearate, glyceryl behenate, magnesium stearate, mineral oil, polyethylene glycol, sodium stearyl fumarate, stearic acid, talc, vegetable oil, and zinc stearate. Filling agents such as lactose, calcium carbonate, calcium phosphate, calcium sulfate, microcrystalline cellulose, dextran, starches, sucrose, xylitol, lactitol, mannitol, sorbitol, sodium chloride, polyethylene glycol, and the like can be used for formulating the pharmaceutical composition as a capsule.

Surfactants that can be used include but are not limited to sodium lauryl sulfate, sorbitan monooleate, polyoxyethylene sorbitan monooleate, bile salts, glyceryl monostearate, PLURONIC® line (BASF), and the like. Solubilizers such as citric acid, succinic acid, fumaric acid, malic acid, tartaric acid, maleic acid, glutaric acid sodium bicarbonate and sodium carbonate and the like can be used. Diluents that may be used include calcium carbonate, calcium phosphate-dibasic, calcium phosphate-tribasic, calcium sulfate, cellulose (microcrystalline or powdered), dextrates, dextrin, fructose, kaolin, lactose, mannitol, sorbitol, starch, and sucrose.

The particle may be coated with a protective layer; however, inclusion of such layer is purely optional. Many ingredients can be incorporated into the overcoating formula, for example to provide a quicker immediate release, such as plasticizers (described above). A protective coating layer may be applied by conventional coating techniques such as pan coating or fluid bed coating using solutions of polymers in water or suitable organic solvents or by using aqueous polymer dispersions. Suitable materials for the protective layer include cellulose derivatives such as hydroxyethyl cellulose, hydroxypropyl cellulose, hydroxypropyl methylcellulose, polyvinylpyrrolidone, polyvinylpyrrolidone/vinyl acetate copolymer, ethyl cellulose aqueous dispersions (AQUACOAT®, SURELEASE®), EUDRAGIT® RL 30D, OPADRY® and the like.

The size of a sphere or a granule particle described herein is selected so that the matrix particles have a diameter in the range of about 50-3500 microns; preferably 100-800 microns. In one embodiment, the size of the particle is mesh size 12.

Release Profile

The pulse release formulation of the present invention is designed to release the surface adhered amount of a drug within about 30 minutes following intake, and the matrix deposited drug after about 1 to about 4 hours. In another embodiment, the matrix-deposited drug is 90% released after a lag of about 1-3 hours following the immediate drug release. The pulse release also includes drug release profiles in which the drug release increases from going from a low pH (e.g. stomach) to a higher pH (e.g. intestines).

Pharmaceutically active ingredient is incorporated into enteric polymer based matrix, which allows for the release of the active ingredient at a certain pH. The addition of a sustained release and enteric polymers allows for time-dependent and pH independent release of the drug. Accordingly, the precise location and timing of the drug release can be controlled by adjusting the ratios of enteric and sustained release polymers. In one embodiment, the matrix can be formulated in such manner to allow a pulse release at a certain pH, i.e. all of the drug in the matrix is released within about 3 hours following the onset of such release. In another embodiment, the drug can be released gradually following the onset of such release at a certain pH. The matrix is formulated to achieve one of the release profiles based on the pharmaceutically active ingredient that is used.

As described above, the timing of the delayed pulse can be controlled by varying the amounts of pH-sensitive, i.e. enteric polymers and time-dependent, i.e. sustained release polymers. By way of example, by increasing the amount of sustained release polymer and decreasing the amount of the enteric polymer, the release of the matrix-containing drug is delayed.

It will also be appreciated that the method of forming the immediate release formulations as described herein, i.e., regranulating the outer surface of the drug is not only applicable for matrices described herein, but for a number of different pharmaceutical formulations, which are solid. For example, layered spheres or granules can also be treated with a hydroalcoholic solvent, dried and regranulated with additional drug prior to formulating them as tablets or capsules. For such applications, it is important that the solvent at least partially dissolves polymer(s) in the sphere, and that the solubility of the polymer is greater that the solubility of the drug in that solvent. A skilled artisan can readily determine the solubility of a particular solvent and a drug in a selected solvent. By way of example, this method may be advantageous for providing an immediate release of an opiate, analgesic, or an anti-inflammatory drug, which is then followed by the delayed release of the already pre-made formulation.

Oral Formulation

For oral administration, the pharmaceutical composition can contain a desired amount of a pharmaceutically active ingredient and be in the form of, for example, a tablet, a hard or soft capsule, a lozenge, a cachet, a dispensable powder, granules, a suspension, an elixir, a liquid, or any other form reasonably adapted for oral administration. Such a pharmaceutical composition is preferably made in the form of a discrete dosage unit containing a predetermined amount of the drug, such as tablets or capsules. Unit dosage tablets or capsules are preferred.

Liquid dosage forms for oral administration can include pharmaceutically acceptable emulsions, solutions, suspensions, syrups, and elixirs containing inert diluents commonly used in the art, such as water. Such compositions can also comprise, for example, wetting agents, emulsifying and suspending agents, and sweetening, flavoring, and perfuming agents. When formulating a liquid dosage, the pharmaceutical composition of the present invention may also contain a non-functional coating, such as OPADRY®. The application of such coating is standard in the pharmaceutical art.

When a drug is formulated as a tablet, a dissolution aid is included in order to disperse the spheres once the tablet is ingested. These materials should be present in the range of from about 3% to about 15% (w/w).

In preparing a tablet, the particles are compressed into a tablet form using a tablet machine typically utilized in the pharmaceutical arts. The particles are generally mixed with disintegrant(s) and lubricant(s) for a set number of minutes to provide a homogeneous blend. Following that, the mixture is fed to the die of a tablet press and sufficient pressure is applied to form a solid tablet. The compression force used is adequate to form a tablet; however, not sufficient to fracture the beads or coatings. The pressure can vary, and typically ranges from about 1,000 psi to about 6,000 psi and preferably about 2,000 psi force. After the tablet is formed, the tablet is coated with materials normally used in pharmaceuticals, if desired. If coated, the coating is prepared by techniques known in the art.

Administration

It will be appreciated that the multiple dosage form of the present invention can deliver rapid and complete dosages of pharmaceutically active amphetamine salts to achieve the desired levels of the drug in a recipient over the course of about 6-8 hours with a single oral administration.

Effective dosage forms, modes of administration and dosage amounts of the composition of the invention may be determined empirically, and making such determinations is within the skill of the art. It is understood by those skilled in the art that the dosage amount will vary with the particular composition employed, the condition being treated, the severity of the condition, the route of administration, the rate of excretion, the duration of the treatment, the identity of any other drugs being administered to the mammal, the age, size and species of the mammal, and like factors well known in the medical and veterinary arts. In general, a suitable daily dose of a compound of the present invention will be that amount which is the lowest dose effective to produce a therapeutic effect. However, the total daily dose will be determined by an attending physician or veterinarian within the scope of sound medical judgment. If desired, the daily dose may be administered in multiple sub-doses, administered separately at appropriate intervals throughout the day.

By way of example, when the pharmaceutically active ingredient is a mixture of amphetamine salts, the pharmaceutical composition is indicated for treatment of attention hyperactivity deficit disorder (ADHD) in children of 3-10 years of age. Such pharmaceutical composition can contain, for example, a mixture of amphetamine salts in the amounts of 2.5 mg, 5 mg, 10 mg, 20 mg, 30 mg, and 40 mg. In one embodiment, the amount of amphetamine salts in the pharmaceutical formulation described herein is 5 mg, 10 mg, 20 mg, or 30 mg.

When the pharmaceutically active ingredient is an opiate, such as morphine, the pharmaceutical composition of the present invention can contain, e.g., 20 mg, 30 mg, 60 mg, or 100 mg of morphine.

Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the present invention.

All publications and patent applications cited in this specification are herein incorporated by reference as if each individual publication or patent application was specifically and individually indicated to be incorporated by reference.

The following examples illustrate the invention, but are not to be taken as limiting the various aspects of the invention so illustrated.

EXAMPLES

Table 1 lists the components and weights thereof used to make a pharmaceutical composition of the present invention, which utilizes dextroamphetamine sulfate (DAS) as the pharmaceutically active ingredient.

TABLE 1

Batch size 100 g (Sample F27A)

| Ingredient | % w/w | weight in grams (g) |
| --- | --- | --- |
| Dextroamphetamine Sulfate (DAS) | 25 | 25* |
| HPMCAS-L | 55 | 55 |
| Triethyl Citrate | 5 | 5 |
| Citric Acid | 7 | 7 |
| ETHOCEL ® Standard FP 10 | 8 | 8 |
| Granulating Solvent Ethanol/Water Ratio | 80/20 | 80/20 |

*25 grams of DAS represents the total amount of the drug; of that, 12.5 grams is in the matrix (referred to in the example as Part 1), and 12.5 grams is on the outer surface of the matrix (referred to in the example as Part 2).

The amount of pharmaceutically active ingredient (DAS) that was needed for the composition was calculated as shown below:

$DAS_{part1}$=w/w % drug (Table 1)*Part 1% Drug Load*batch size (g)=0.25*0.5*100=12.5 g $DAS_{part2}$=w/w % drug (Table 1)*Part 2% Drug Load*batch size (g)=0.25*0.5*100=12.5 g The pharmaceutical composition described in Table 1 was prepared as follows:

1. Ethanol and distilled water were combined in a beaker as per the ratio listed in Table 1 for each 100 mL of granulating solvent prepared.
2. The granular citric acid was powdered to fine powder in a grinder.
3. 5 mL of TEC was volumetrically pipetted into 35 mL of granulating solvent and citric acid was added.
4. ETHOCEL, HPMCAS-L $DAS_{part1}$ were added to a mixer and the dry mixture was blended.
5. TEC/Citric Acid solution was added to the dry mixture from step 4 in increments, and the whole mixture was granulated/blended in the mixer.
6. Granulating was continued using dropwise addition of sufficient granulating solvent to obtain a compact mass. Volume of solvent used was recorded.
7. The excipient mass from step 6 was passed through the mill to obtain string extrudates. (if extrudates cannot be formed in this manner, a grinder may be utilized.)
8. String extrudates were dried in the hood overnight, following which the extrudates were passed through a sieving screen or grinder as needed to obtain granules.
9. The granules were sieved through #10, #12, #16, #20 mesh, documenting the amount collected in each sieve.
10. The mesh #12 granules were used in further experiments, in which DAS was adhered to the outer surface of the granules.
11. The mesh #12 granules and $DAS_{part2}$ were weighed and transferred to a mixing bowl.
12. The mixture from step 11 was re-granulated by spraying with granulating solvent and mixing until the granulation process was completed. The mass of solvent used was recorded.
13. The mixing was continued for approximately 2 minutes after the addition of solvent was complete, following which the granules were transferred to wax paper to dry overnight in the hood.
14. The granules were sieved and collected in #12 mesh size for dissolution study.
15. A continuum dissolution study was performed at the following pH values: 1.2, 5.5, and 6.8.
16. The dissolution study was performed using USP dissolution Apparatus I with baskets.
17. The granules from step 14 were kept in dissolution vessels having pH 1.2, 5.5, and 6.8 for 1 hour each, and the dissolution medium was maintained at 37° C. throughout the dissolution study.
18. At time points indicated in FIG. 1, the vessel samples were collected, and the amount of the dissolved drug was analyzed using HPLC.

The results of the dissolution study are shown in FIG. 1.

The invention claimed is:

1. An oral pharmaceutical composition consisting of (i) a polymer matrix consisting of a mixture of at least one enteric polymer, at least one sustained release polymer, an optional plasticizer, an optional binder, and a first pharmaceutically active ingredient distributed substantially uniformly throughout the polymer matrix, and (ii) a population of discrete particles adhering to the outer surface of the polymer matrix, the population of discrete particles consisting of a second pharmaceutically active ingredient and having a size from about 500 nanometers to about 800 microns, wherein the oral pharmaceutical composition has a pulse release profile.

2. The oral pharmaceutical composition of claim 1 wherein the first and second pharmaceutically active ingredients are the same.

3. The oral pharmaceutical composition of claim 1, wherein the discrete particles adhering to the outer surface of the polymer matrix range from about 50 microns to about 200 microns.

4. The oral pharmaceutical composition of claim 1, wherein the at least one enteric polymer is present in an amount from about 30% w/w to about 80% w/w of the polymer matrix.

5. The oral pharmaceutical composition of claim 4, wherein the amount of the at least one enteric polymer is about 55% w/w of the polymer matrix.

6. The oral pharmaceutical composition of claim 1, wherein the at least one sustained release polymer is present in an amount from about 5% w/w to about 80% w/w of the polymer matrix.

7. The oral pharmaceutical composition of claim 6, wherein the amount of the at least one sustained release polymer is about 5% w/w of the polymer matrix.

8. The oral pharmaceutical composition of claim 1, wherein the at least one enteric polymer is selected from the group consisting of hydroxypropyl methylcellulose acetate succinate (HPMCAS), hydroxypropyl methylcellulose phthalate (HPMCP), polyvinyl acetate phthalate, cellulose acetate phthalate, cellulose acetate trimellitate, shellac, polymethacrylates containing carboxyl groups, amylose acetate phthalate, styrene maleic acid copolymer, cellulose acetate succinate, and combinations thereof.

9. The oral pharmaceutical composition of claim 8, wherein the at least one enteric polymer is HPMCAS.

10. The oral pharmaceutical composition of claim 1, wherein the at least one sustained release polymer is selected from the group consisting of ethyl cellulose, trimethylammoniumethyl methacrylate chloride, 30% by weight dispersion of poly(ethylacrylat-methylmethacrylat), hydroxypropyl methylcellulose (HPMC), hydroxyethyl cellulose (HEC), polyvinylpyrrolidone (PVP), and combinations thereof.

11. The oral pharmaceutical composition of claim 10, wherein the at least one sustained release polymer is ethyl cellulose.

12. The oral pharmaceutical composition of claim 2, wherein the first and second pharmaceutically active ingredients in combination are present in the composition in the amount of about 25% w/w.

13. The oral pharmaceutical composition of claim 2, wherein the first and second pharmaceutically active ingredients are amphetamine salts or the first and second pharmaceutically active ingredients are opiate drugs.

14. The oral pharmaceutical composition of claim 13, wherein the first and second pharmaceutically active ingredients are a mixture of amphetamine salts.

15. The oral pharmaceutical composition of claim 14, wherein the mixture of amphetamine salts is a mixture of neutral salts of dextroamphetamine sulfate, amphetamine sulfate, the dextro isomer of amphetamine saccharate, and d,l-amphetamine aspartate.

16. The oral pharmaceutical composition of claim 1, wherein about 50% by weight of the total amount of the first and second pharmaceutically active ingredients is present in the polymer matrix and about 50% by weight of the total amount of the first and second pharmaceutically active ingredients is present in the population of discrete particles adhering to the outer surface of the polymer matrix.

17. The oral pharmaceutical composition of claim 16, wherein the first and second pharmaceutically active ingredients are the same.

18. The oral pharmaceutical composition of claim 17, wherein the first and second pharmaceutically active ingredients are a mixture of amphetamine salts.

19. The oral pharmaceutical composition of claim 18, wherein the mixture of amphetamine salts includes a mixture of neutral salts of dextroamphetamine sulfate, amphetamine sulfate, the dextro isomer of amphetamine saccharate, and d,l-amphetamine aspartate.

20. The oral pharmaceutical composition of claim 2, wherein the optional plasticizer and the optional binder are present in the polymer matrix.

21. The oral pharmaceutical composition of claim 20, wherein the plasticizer is selected from the group consisting of acetyltriethyl citrate, triethyl citrate, acetyltributyl citrate; dibutylsebacate, triacetin, polyethylene glycols, propylene glycol, and combinations thereof.

22. The oral pharmaceutical composition of claim 21, wherein the plasticizer is triethyl citrate.

23. The oral pharmaceutical composition of claim 20, wherein the binder is selected from the group consisting of citric acid, acacia, alginic acid, carboxymethylcellulose sodium, microcrystalline cellulose, dextrin, ethylcellulose, gelatine, glucose, guar gum, hydroxypropyl methylcellulose, methylcellulose, polyethylene oxide, povidone, pregelatinised starch, syrup, polyvinylpyrrolidone, polyvinylpyrrolidone/vinyl acetate copolymer, and combinations thereof.

24. The oral pharmaceutical composition of claim 23, wherein the binder is methylcellulose.

25. The oral pharmaceutical composition of claim 1, wherein the outer surface of the polymer matrix is treated with a granulating solvent prior to depositing the second pharmaceutically active ingredient as the population of discrete particles thereon.

26. The oral pharmaceutical composition of claim 25, wherein the granulating solvent is a hydroalcoholic solvent.

27. The oral pharmaceutical composition of claim 16, wherein the hydroalcoholic solvent contains about 80% ethanol and about 20% water.

* * * * *

UNITED STATES PATENT AND TRADEMARK OFFICE
CERTIFICATE OF CORRECTION

PATENT NO.           : 9,713,592 B2
APPLICATION NO.      : 11/909270
DATED                : July 25, 2017
INVENTOR(S)          : Ashwini Gadre et al.

Page 1 of 1

It is certified that error appears in the above-identified patent and that said Letters Patent is hereby corrected as shown below:

In the Claims

Column 14, Line 51, Claim 27: "claim 16" should read -- claim 26 --.

Signed and Sealed this
Twenty-third Day of January, 2018

Joseph Matal
*Performing the Functions and Duties of the
Under Secretary of Commerce for Intellectual Property and
Director of the United States Patent and Trademark Office*